US007102037B2

(12) United States Patent
Levin et al.

(10) Patent No.: US 7,102,037 B2
(45) Date of Patent: Sep. 5, 2006

(54) SELECTIVE DECOMPOSITION OF ETHERS

(75) Inventors: Doron Levin, Annandale, NJ (US); Shifang Luo, Pittsford, NY (US); James Clarke Vartuli, Schwenksville, PA (US); Charles Morris Yarbrough, Baton Rouge, LA (US); Dane Clark Grenoble, Houston, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 116 days.

(21) Appl. No.: 11/013,482

(22) Filed: Dec. 16, 2004

(65) Prior Publication Data

US 2005/0177009 A1  Aug. 11, 2005

Related U.S. Application Data

(60) Provisional application No. 60/532,381, filed on Dec. 23, 2003.

(51) Int. Cl.
*C07C 33/02* (2006.01)
(52) U.S. Cl. ...................................... 568/908; 585/640
(58) Field of Classification Search ................ 568/908; 585/640
See application file for complete search history.

(56) References Cited

U.S. PATENT DOCUMENTS

| 4,254,290 | A | 3/1981 | Chambers et al. | 568/866 |
| 4,320,232 | A | 3/1982 | Volkamer et al. | 585/697 |
| 4,357,147 | A | 11/1982 | Bezman | 44/56 |
| 4,398,051 | A | 8/1983 | Araki et al. | 585/640 |
| 4,521,638 | A | 6/1985 | Kida et al. | 585/640 |
| 4,691,073 | A | 9/1987 | Michaelson | 585/639 |
| 5,117,920 | A | 6/1992 | Soble | 173/28 |
| 5,171,920 | A | 12/1992 | Chaumette et al. | 585/640 |
| 5,177,301 | A | 1/1993 | Knifton | 585/855 |
| 5,254,785 | A | 10/1993 | Rosenfeld et al. | 585/640 |
| 5,607,892 | A | 3/1997 | Chopin et al. | 502/304 |
| 6,124,232 | A | 9/2000 | Chang et al. | 502/308 |
| 6,150,299 | A | 11/2000 | Umemoto et al. | 502/304 |
| 6,162,757 | A | 12/2000 | Chang et al. | 502/302 |
| 6,297,406 | B1 | 10/2001 | Levin et al. | 568/798 |

FOREIGN PATENT DOCUMENTS

| JP | 59010528 | | 1/1984 |
| JP | 6072904 | | 3/1994 |
| JP | 06072904 A | * | 3/1994 |
| WO | WO 96/13328 | | 9/1996 |
| WO | WO 03/037506 | | 5/2003 |

OTHER PUBLICATIONS

P. B. Meunier et al., "Production D'isobutene de Haute Purete' Par Decomposition Du MTBE," Revue Del'Institut Francais Du Petrole, vol. 46, No. 3, pp. 360-387, (1991).
Convers, A. et al. "Make Pure Butenes Via MTBE", *Hydrocarbon Processing*, p. 95-98, Mar., (1981).
P.B. Meunier et al., "Production D'isobutene de Haute Purete'Par Decomposition Du MTBE," Revue Del'Institut Francais Du Petrole, vol. 46, No. 3, pp. 360-387, (1991) (*Translation attached for Examiner's Consideration*).

* cited by examiner

*Primary Examiner*—Samuel L. Barts
*Assistant Examiner*—Kellette Gale
(74) *Attorney, Agent, or Firm*—Andrew B. Griffis

(57) ABSTRACT

A process for selectively converting a dialkyl ether to the corresponding alkene and alkanol comprises contacting a feed containing at least one dialkyl ether with a catalyst comprising a mixed metal oxide which comprises at least one metal selected from Group 4 of the Periodic Table of Elements and at least one metal selected from Group 3 (including the Lanthanides and Actinides) and Group 6 of the Periodic Table of Elements.

45 Claims, No Drawings

SELECTIVE DECOMPOSITION OF ETHERS

CROSS REFERENCE TO RELATED APPLICATIONS

This application claims the benefit of priority under 35 U.S.C. 119(e) to U.S. Provisional Application Ser. No. 60/532,381, filed Dec. 23, 2003.

FIELD

This invention relates to the selective decomposition of ethers to the corresponding alkenes and alkanols.

BACKGROUND

The conversion of ethers to their corresponding alkenes and alkanols is an important reaction in a number of commercial processes. Thus, for example, this reaction is used to remove ethers, such as isopropyl ether, produced as the by-products of other processes, such as the hydration of propylene to produce isopropanol. In addition, an important route for the production of tertiary olefins involves reaction of mixed olefins with an alcohol over an acid catalyst to selectively produce a tertiary alkyl ether, separation of the ether from the remaining olefin stream, and then decomposition of the ether to the desired tertiary olefin. This latter process relies on the fact that tertiary olefins react with alcohols more rapidly than either secondary or primary olefins and hence provides an effective method for extracting tertiary olefins, such as isobutene and isoamylene, from a mixed olefin stream. For the purposes of this invention, a tertiary olefin or isoolefin will be understood to be an olefin containing at least one carbon atom that is covalently bonded to three other carbon atoms.

One commercial process for the selective decomposition of ethers, such as methyl tert-butyl ether (MTBE), is disclosed in U.S. Pat. No. 4,691,073 and employs a fluoride-treated clay, such as hydrofluoric acid (HF) treated attapulgite (HFA), as the catalyst. The process is typically operated at a starting temperature of about 340° F. (170° C.) but, since the catalyst loses its activity rapidly, run times are normally very short and the temperature has to be increased during the run to a final value of about 380° F. (193° C.) in order to maintain a constant MTBE conversion, typically around 90%. In fact, the cycle length of the HFA catalyst normally ranges from only a few weeks to 30+ days, which is a major disadvantage in that the loss of catalyst activity results in considerable losses in production time and leads to high catalyst replacement and disposal costs. Moreover, the relatively high temperatures required by the HFA catalyst tends to increase the concentration of impurities such as dimethyl ether (DME) and isobutane in the product, as well as promoting side reactions, for example, diisobutylene dehydrocyclization and isobutene oligomerization and polymerization, that lead to fouling of the catalyst.

Other solid acids have been proposed for the selective decomposition of tert-alkyl ethers to tertiary olefins. For example, U.S. Pat. No. 4,254,290 describes the use of solid acids such as $SiO_2/Al_2O_3$, $WO_3/Al_2O_3$, $H_2SO_4$-treated clay and acidic ion-exchange resins as catalysts for the decomposition of tert-alkyl ether alkanols. In U.S. Pat. Nos. 4,320,232 and 4,521,638, phosphoric acid on various supports is described as a catalyst suitable for the decomposition of tert-butyl alkyl ethers to isobutene and alcohols. The use of silica supported aluminum compounds as catalysts for the decomposition of alkyl tert-alkyl ethers is described in U.S. Pat. No. 4,398,051, whereas intermediate pore zeolites, such as ZSM-5 are employed for this purpose in U.S. Pat. No. 4,357,147.

An extensive discussion of catalysts for, and the mechanism of, the conversion of MTBE to isobutene is provided in an article entitled "Production D'Isobutene de Haute Puretépar Décomposition du MTBE" by P. B. Meunier et al. in Revue de L'Institut Francais du Petrole, vol. 46, No. 3, May 19991, pages 361 to 387. This document mentions the use of sulfonic resins, supported phosphoric acid, zeolites, silico-aluminas and modified silico-aluminas as catalysts for MTBE decomposition. According to this document, side-reactions can be limited by controlling the surface of the catalyst, its activity and the presence of impurities that can increase or decrease the catalyst acidity.

It is also known from, for example, U.S. Pat. No. 5,254,785, to employ calcium-exchanged zeolite Y as a catalyst in the conversion of dialkyl ethers to olefins. However, although pilot plant studies indicated that this catalyst would have a significantly lower aging rate than the HFA catalyst, the improved performance of the Ca—Y catalyst has to date never been achievable on a commercial scale.

U.S. Pat. No. 5,177,301 describes a two-step method for separating isobutylene from a $C_4$ hydrocarbon fraction comprising (a) contacting the $C_4$ fraction containing isobutylene with a glycol in the presence of a catalyst comprising a heteropoly acid on an inert support at a temperature of about 60° C. to 160° C. thereby reacting the isobutylene with the glycol to yield a glycol mono-t-butyl ether, and subsequently (b) reacting the glycol mono-t-butyl ether over the heteropoly acid on an inert support at a temperature of 150° C. to 220° C. to produce the separated isobutylene. Suitable heteropoly acids include 12-tungstophosphoric acid, 12-molybdophosphoric acid, molybdosilicic acid and 12-tungstosilicic acid on an inert support, such as silica, alumina, titania and zirconia.

U.S. Pat. No. 5,171,920 describes a process for obtaining a tertiary olefin, e.g. isobutylene, by decomposing the corresponding ether, e.g. methyl tert-butyl ether, in the presence of a catalyst comprising a silica support modified by the addition of at least one element or selected from the group constituted by rubidium, cesium, magnesium, calcium, strontium, barium, gallium, lanthanum, cerium, praseodymium, neodymium and uranium and optionally by the addition of at least one element selected from the group constituted by aluminum, titanium and zirconium. Modification of the silica support is effected by impregnating the support with at least one aqueous solution (or a solution in at least one appropriate solvent) containing the modifying element or elements it is desired to introduce.

Japanese Published Patent Application No. JP-A-06072904, published Mar. 15, 1994, describes a process for obtaining a tertiary olefin by decomposing the corresponding alkyl tert-alkyl ether over a catalyst composition having the formula $Si_aAl_bZr_cX_dO_e$ where X is an element selected from sodium, potassium, cesium, cerium, zinc, magnesium and calcium; a, b, c, d and e are the atomic ratios of their respective elements and when a is 1, b is 0.01–1, c is 0.001–1, d is 0.001–1 and e designates the number of oxygen atoms necessary to satisfy the valence of the other components.

In addition, Japanese Published Patent Application No. JP-A-59010528, published Jan. 20, 1984, describes a process for thermally decomposing a tertiary ether to a tertiary olefin in the presence of a titanium or zirconium oxide catalyst containing 0.1 to 20 wt % of $SO_4$ groups. The catalyst activity is said to be high even at low temperatures thereby allowing co-production of the corresponding alcohol with negligible etherification.

It has now been found that certain mixed metal oxides comprising at least one metal from Group 4 of the Periodic Table of Elements, at least one metal from Group 3 (including the Lanthanides and Actinides) and Group 6 of the Periodic Table of Elements, and optionally at least one metal from Groups 7, 8, and 11 of the Periodic Table of Elements exhibit both high selectivity and long catalyst lifetime when used as ether decomposition catalysts.

U.S. Pat. No. 5,607,892 discloses a zirconium/cerium mixed oxide having a specific surface area of greater than 10 m$^2$/g. The mixed oxide is produced by intimately admixing a zirconium sol with a cerium sol, wherein the ratio of the mean diameter $r_1$ of the particles of the zirconium sol to the mean diameter $r_2$ of the particles of the cerium sol is at least 5, adding a precipitating amount of a base, such as aqueous ammonia, sodium hydroxide, or potassium hydroxide to the mixture, recovering the precipitate thus formed and calcining the precipitate at a temperature of 700 to 1,000° C. The mixed oxide is said to be useful as a catalyst or catalyst support for carrying out a variety of reactions, such as dehydration, hydrosulfurization, hydrodenitrification, desulfurization, hydrodesulfurization, dehydrohalogenation, reforming, steam reforming, cracking, hydrocracking, hydrogenation, dehydrogenation, isomerization, dismutation, oxychlorination, dehydrocyclization of hydrocarbons or other organic compounds, oxidation and/or reduction reactions, the Claus reaction, treatment of exhaust gases emanating from internal combustion engines, demetallation, methanation or shift conversion.

U.S. Pat. No. 6,150,299 discloses a cerium- and zirconium-based mixed oxide containing sulfur, which is said to be active as an exhaust gas purification catalyst and which comprises 50 to 79% by weight cerium oxide, 20 to 49% by weight zirconium oxide and 1 to 5% by weight sulfate ($SO_4$). In Example 1, the mixed oxide was produced by dispersing cerous sodium sulfate double salt (containing 75 g as cerium oxide) in 1,000 g of water and adding an aqueous solution of zirconium nitrate (containing 25 g as zirconium oxide). Then, an aqueous solution of sodium hydroxide was added until the pH of the mixture became 13.5, whereby a precipitate was obtained. This precipitate was separated from the mixture and heated in the air at 600° C. for 5 hours. Analysis showed the resultant mixed oxide to contain 73.9% by weight cerium oxide, 24.1% by weight zirconium oxide and 2.0% by weight sulfate.

International Patent Publication No. WO 03/37506, published May 8, 2003, discloses a promoter or catalyst support for an automobile exhaust gas system comprising a zirconium-cerium-based mixed oxide produced by reacting an alkali with an aqueous solution of a zirconium salt containing 0.42–0.7 mole of sulfate anion per mole of zirconium cation at a temperature not greater than 50° C. in the presence of a cerium salt to form a mixed cerium-zirconium hydroxide and then calcining the hydroxide at a temperature of 500 to 1000° C., such as 650 to 850° C.

U.S. Pat. No. 6,124,232 discloses a tungsten-modified zirconia catalyst produced by coprecipitating zirconia with an anion or oxyanion of tungsten in the presence of ammonium sulfate to obtain a sulfate-containing product, steaming the sulfate-containing product; recovering the sulfate-containing product by filtration, washing the product with water in order to remove the sulfate ions and calcining the product to produce a catalyst that is essentially free of sulfate ions. The catalyst is said to be active in the isomerization of paraffins.

U.S. Pat. No. 6,162,757 discloses a synthesis of a solid acid containing zirconium, in addition to a rare earth element, such as cerium, useful for isomerization of paraffins, ring opening of cyclics, hydrocracking, alkylation, hydrogenation of polynuclear aromatics, selective catalytic reduction of nitrogen peroxides, and oligomerization of light olefins.

U.S. Pat. No. 6,297,406 discloses a process for producing phenol and acetone from cumene hydroperoxide, in which cumene hydroperoxide is contact with a solid acid catalyst comprising a mixed oxide of cerium and a Group IVB metal.

SUMMARY

In one aspect, the present invention resides in a process for selectively converting a dialkyl ether to the corresponding alkene and alkanol comprising contacting a feed containing at least one dialkyl ether with a catalyst comprising an acidic mixed metal oxide having the following composition:

where X is at least one metal selected from Group 4 of the Periodic Table of Elements, Y is at least one metal selected from Group 3 (including the Lanthanides and Actinides) and Group 6 of the Periodic Table of Elements, and Z is at least one metal selected from Groups 7, 8, and 11 of the Periodic Table of Elements; m, n, p and q are the atomic ratios of their respective components and, when m is 1, n is from about 0.01 to about 0.75, p is from 0 to about 0.1, and q is the number of oxygen atoms necessary to satisfy the valence of the other components.

Conveniently, said mixed metal oxide contains up to 5wt %, such as up to 1 wt %, sulfur, typically present as sulfate. In such case, the mixed metal oxide is of the formula $X_mY_nZ_pO_qS_r$ where X, Y, Z, m, n, p, and q have the same meaning as above, S is sulfur, and r ranges from 0.03 to 0.5, such as from 0.04 to 0.4, advantageously from 0.05 to 0.36. When the mixed metal oxide is of formula $X_mY_nZ_pO_qS_r$ it is preferred that p=0, and even more preferred if X is zirconium and Y is cerium.

In another aspect, the invention resides in a process for selectively converting a dialkyl ether to the corresponding alkene and alkanol comprising contacting a feed containing at least one dialkyl ether with a catalyst comprising an acidic mixed metal oxide which comprises at least one metal selected from Group 4 of the Periodic Table of Elements and at least one metal selected from Group 3 (including the Lanthanides and Actinides) and Group 6 of the Periodic Table of Elements and which is produced by co-precipitating oxide precursors of said metals from a liquid medium and then calcining the co-precipitate.

Conveniently, said liquid medium also contains sulfate ions.

Conveniently, said calcining is conducted at a temperature of at least 400° C., such as at least 500° C., for example about 500° C. to about 800° C., and as a further example about 600° C. to about 700° C.

Conveniently, said oxide precursors are precipitated from said solution at a pH less than 12, such as about 6 to about 11, preferably about 7 to about 10.

Preferably, said at least one Group 4 metal comprises zirconium.

Preferably, said at least one metal selected from Group 3 and Group 6 comprises cerium, molybdenum, or tungsten.

Preferably, said mixed metal oxide catalyst also contains a further metal selected from Groups 7, 8, and 11 of the Periodic Table of Elements, such as iron, manganese, or copper.

Typically, said contacting is conducted at a temperature of about 50° C. to about 320° C., such as about 100° C. to about 275° C., or about 125° C. to about 250° C. Typically said contacting is conducted at a pressure of about 0 kPa to about 3500 kPa, such as about 0 kPa to about 2400 kPa, or about 100 kPa to about 1400 kPa. Typically said contacting is conducted at a weight hourly space velocity (WHSV) of about 0.1 hr$^{-1}$ to about 25 hr$^{-1}$, such as about 0.5 hr$^{-1}$ to about 10 hr$^{-1}$.

The process of the invention achieves a high level of conversion of ethers to selectively produce the corresponding olefins and alcohols and/or exhibits an enhanced cycle life as compared with the process using a prior art catalyst, such as HFA.

DETAILED DESCRIPTION OF THE EMBODIMENTS

Introduction

The present invention is directed to a process for the selective decomposition of ethers to the corresponding olefins and alcohols. In one embodiment, the process employs a tert-alkyl ether, such as methyl tert-butyl ether (MTBE) or tert-amyl methyl ether (TAME), to produce iso-olefins, such as iso-butene and iso-amylene, in high yield. In another embodiment, the process converts dialkyl ether by-products, such as sec-butyl ether (SBE) and iso-propyl ether (IPE), also known as di-isopropyl ether (DIPE), of olefin hydration reactions to higher value products, such as the olefin starting materials and alcohols.

Mixed Metal Oxide Catalyst Composition

The mixed metal oxide composition used as the catalyst in the process of the invention comprises at least one first metal selected from Group 4 of the Periodic Table of Elements and at least one second metal selected from Group 3 (including the Lanthanides and Actinides) and Group 6 of the Periodic Table of Elements. It is to be appreciated that Periodic Table of Elements referred to herein is the IUPAC version described in the *CRC Handbook of Chemistry and Physics*, 78th Edition, CRC Press, Boca Raton, Fla. (1997).

Suitable Group 4 metals include titanium, zirconium and hafnium, with zirconium being most preferred. Suitable Group 3 metals include scandium, yttrium and lanthanum, and metals from the Lanthanide or Actinide series, such as cerium, praseodymium, neodymium, samarium, europium, gadolinium, terbium, dysprosium, holmium, erbium, thulium, ytterbium, lutetium and thorium. The most preferred Group 3 metal is cerium. Suitable Group 6 metals include chromium, molybdenum, and tungsten, with tungsten being most preferred. The first and second metal species present in the final catalyst are not limited to any particular valence state and may be present in any positive oxidation value possible for the respective species.

Other metals, such as metals of Groups 7, 8, and 11 of the Periodic Table of Elements, for example iron, manganese, and/or copper, may optionally be added to the present catalyst to alter its catalytic properties.

In one embodiment, the mixed metal oxide catalyst composition of the invention has the following empirical formula:

where X is at least one metal selected from Group 4 of the Periodic Table of Elements, Y is at least one metal selected from Group 3 (including the Lanthanides and Actinides) and Group 6 of the Periodic Table of Elements, and Z is at least one metal selected from Groups 7, 8, and 11 of the Periodic Table of Elements; m, n, p and q are the atomic ratios of their respective components and, when m is 1, n is from about 0.01 to about 0.75, such as from about 0.02 to about 0.6; p is 0 to about 0.1, such as from about 0 to about 0.05; and q is the number of oxygen atoms necessary to satisfy the valence of the other components. Thus in this embodiment, the mixed metal oxide compositions do not contain the silicon and/or aluminum present in the prior art catalysts disclosed in, for example, U.S. Pat. No. 5,171,920 and Japanese Published Patent Application No. JP-A-06072904.

The mixed metal oxide composition employed in the process of the invention is produced by chemical interaction of a Group 4 metal oxide with an oxide or oxyanion of a Group 3 and/or 6 metal. The catalysts selected for the purposes of the present invention exhibit very selectivity for ether decomposition, while minimizing side-reactions. While the authors do not wish to be bound by any theory, it seems that the selection of the particular metal elements and/or their relative ratios and/or the presence of sulfur, such as in specific amounts, provide acidic properties particularly well suited for ether decomposition.

The mixed oxides used in the process of the present invention preferably contains sulfur, conveniently provided by the presence of sulfate ions in the precursor mixture. Sulfur is typically present in an amount of up to 5 wt %, such as up to 1 wt %, of the final mixed oxide composition.

The present mixed metal oxides may be composited with an inactive matrix material to form the finished form of the catalysts and for this purpose conventional matrix materials such as alumina and silica are suitable with preference given to silica as a non-acidic binder. Other binder materials may be used, for example, titania, zirconia and other metal oxides or clays. If a matrix is used, the active catalyst may be composited with the matrix in amounts from 90:10 to 10:90 by weight, e.g., from 80:20 to 20:80, or from 70:30 to 30:70 active catalyst:matrix. Compositing may be done by conventional means including mulling the materials together followed by extrusion or pelletizing into the desired finished catalyst particles.

Synthesis of the Mixed Metal Oxide Catalyst Composition

In one embodiment, the catalyst composition may be prepared by impregnation, for example by impregnation of a hydrothermally treated hydrated oxide of the Group 4 metal with an aqueous solution containing a source of ions of a Group 3 and/or Group 6 metal, followed by drying. The resulting catalyst precursor is then calcined in the manner described below.

In such an embodiment, a preferred source of the Group 4 metal oxide is hydrated zirconia. The expression, hydrated zirconia, is intended to connote a material comprising zirconium atoms covalently linked to other zirconium atoms via bridging oxygen atoms and further comprising available surface hydroxyl groups. Without being limited to any particular theory, the available surface hydroxyl groups are believed to react with the Group 3 and/or Group 6 species to form the present acidic catalyst component. Hydrated zirconia can be formed by precalcination of Zr(OH)$_4$ at a temperature of about 100° C. to about 400° C.

Preferably, the hydrated Group 4 metal oxide, such as hydrated zirconia, is subjected to an initial hydrothermal treatment to promote the interaction with the Group 3 and/or Group 6 metal species. The hydrothermal treatment conditions may include a temperature of at least 80° C., e.g., at least 100® C. The hydrothermal treatment may take place in a sealed vessel at greater than atmospheric pressure. However, a preferred mode of treatment involves the use of an open vessel under reflux conditions. Agitation of hydrated Group 4 metal oxide in the liquid medium, e.g., by the action of refluxing liquid and/or stirring, promotes the effective interaction of the hydrated oxide with the liquid medium. The duration of the contact of the hydrated oxide with the liquid medium may be at least 1 hour, e.g., at least 8 hours. The liquid medium for this treatment may have a pH of about 7 or greater, e.g., 9 or greater. Suitable liquid media include water, hydroxide solutions (including hydroxides of $NH_4^+$, $Na^+$, $K^+$, $Mg^{2+}$, and $Ca^{2+}$), carbonate and bicarbonate solutions (including carbonates and bicarbonates of $NH_4^+$, $Na^+$, $K^+$, $Mg^{2+}$, and $Ca^{2+}$), pyridine and its derivatives, and alkyl/hydroxyl amines.

Where the catalyst composition also contains a further metal selected from Groups 7, 8 and 11 of the Periodic Table of Elements, the further metal can be incorporated in the catalyst by impregnation at the same time as or separately from the impregnation with the Group 3 and/or Group 6 metal.

Suitable sources of ions of the Group 3 and/or Group 6 metal and said further metal include compounds such as oxychlorides, chlorides, alkoxides, sulfates and nitrates. Preferably, the Group 3 and/or Group 6 metal is present as a sulfate.

In another, more preferred embodiment, the catalyst is prepared by co-precipitation from a liquid mixture containing a source of Group 4 metal ions and a source of Group 3 and/or Group 6 metal ions followed by calcination of the resulting catalyst precursor in the manner described below. The liquid mixture can be prepared by combining a first liquid solution comprising a source of Group 4 metal ions with a second liquid solution comprising a source of Group 3 and/or Group 6 metal ions, wherein the combination takes place under conditions sufficient to cause co-precipitation of the catalyst precursor as a solid from the liquid medium. Alternatively, the source of the Group 4 metal ions and the source of the Group 3 and/or Group 6 metal ions may be combined into a single solution. This solution may then be subjected to conditions sufficient to cause co-precipitation of the catalyst, such as by the addition of a precipitating reagent, such as ammonium hydroxide, to the solution. Water is a preferred solvent for these solutions.

The pH at which the liquid mixture is maintained during co-precipitation appears to affect the activity of the final catalyst and hence the pH is preferably maintained at or below 9, such as between 3 and 9, for example between 6 and 9. The temperature at which the liquid mixture is maintained during the co-precipitation is generally less than about 200° C., such as from about 30° C. to about 100° C. The resulting gel is preferably then hydrothermally treated at temperatures of at least 80° C., preferably at least 100° C. The hydrothermal treatment typically takes place in a vessel at atmospheric pressure. The gel, in one embodiment, is hydrothermally treated for up to 10 days, such as up to 5 days, for example up to 3 days. The hydrated precursor to the metal oxide(s) is then recovered, for example by filtration or centrifugation, washed, dried and then calcined as described below.

Where the catalyst composition also contains a further metal selected from Groups 7, 8 and 11 of the Periodic Table of Elements, the further metal can be incorporated in the catalyst during coprecipitation of the oxide precursor of the Group 4 metal and the Group 3 and/or Group 6 metal.

Again, suitable sources of the metal ions for the coprecipitation include compounds such as oxychlorides, chlorides, alkoxides, sulfates and nitrates. Preferably, at least one of the metals is present as a sulfate and/or a source of sulfate ions is added to the liquid mixture from which the catalyst precursor is precipitated. Where the Group 4 metal includes zirconium, the preferred source of zirconium is zirconium nitrate, and where the Group 3 metal includes cerium, the preferred source of cerium is a cerium sulfate.

Calcination of the catalyst precursor is effected, typically in an oxidizing atmosphere, at a temperature of at least 400° C., such as at least 500° C., for example from about 500° C. to about 800° C. The calcination time may be up to 48 hours, such as for about 0.5 to about 24 hours, for example for about 1 to about 10 hours. Where the catalyst precursor contains sulfate ions, the calcination conditions should be controlled so as to retain the desired sulfur level in the final catalyst composition.

Ether Decomposition Process

The ether decomposition process of the invention involves contacting an ether-containing feed with a mixed metal oxide catalyst described above under conditions effective to convert the ether to an olefin and an alcohol. Suitable ethers for use in the process of the invention include those having the formula

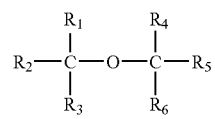

wherein $R_1$, $R_2$, $R_3$, $R_4$, $R_5$ and R6 are the same or different and are selected from hydrogen, alkyl, arylalkyl and alkylaryl species, each preferably having up to 20 carbon atoms.

In general, the conditions employed are not narrowly defined and depend not only on the ether starting material but also on the desired conversion rate and product selectivity. Typically, however, the conditions will include a temperature of about 50° C. to about 320° C., a pressure of about 0 kPa to about 3500 kPa, and a weight hourly space velocity (WHSV) of about 0.1 $hr^{-1}$ to about 25 $hr^{-1}$; such as a temperature of about 100° C. to about 275° C., a pressure of about 0 kPa to about 2400 kPa and a weight hourly space velocity (WHSV) of about 0.5 $hr^-$ to about 10 $hr^{-1}$.

In one practical embodiment, the ether-containing feed contains methyl tert-butyl ether (MTBE) and is produced by reacting a mixed butene stream with methanol. After separation, the present process is used to selectively decompose the resultant MTBE to iso-butene and methanol. A similar process can be used with mixed pentenes to produce tert-amyl methyl ether (TAME) for selective conversion to isoamylene and methanol. In this embodiment, suitable ether decomposition conditions include a temperature of about 1 00° C. to about 200° C. and a pressure of about 0 kPa to about 1000 kPa and a weight hourly space velocity (WHSV) of about 1 $hr^{-1}$ to about 10 $hr^{-1}$.

In another practical embodiment, the ether-containing feed contains isopropyl ether (IPE) and is produced as a by-product of propylene hydration, in a process for the manufacture of isopropyl alcohol (IPA). Some IPA processes involve contacting propylene with sulfuric acid. This can be accomplished with gas/liquid absorption or liquid/liquid extraction. While these processes have been utilized for several decades, some improvements have been made. The improvements include a process configuration that utilizes a unique combination of plug flow, bubble column, and closed stirred tank reactor reaction sections to achieve high conversion of dilute or concentrated propylene. Also spargers custom designed for the propylene/sulfuric acid absorption/extraction section can be used. Further, loop reactors may be preferred to improve mixing integrity.

One possible method of disposal of IPE produced as a side-product of IPA is as a fuel but, not only may this be subject to environmental regulation, but also a higher economic value can be achieved by selective decomposition of the IPE to propylene and IPA. The optimal pathway for this reaction is therefore shown by reaction (1):

$$(CH_3CHCH_3)-O-(CH_3CHCH_3) \rightarrow CH_3CHOHCH_3 + CH_3CH=CH_2 \quad (1)$$

The challenge faced in the catalytic decomposition of IPE is two-fold, firstly, minimizing the dehydration of IPA formed by reaction (1) to propylene according the reaction (2):

$$CH_3CHOHCH_3 \rightarrow CH_3CH=CH_2 + H_2O \quad (2)$$

and secondly, minimizing oligomerization of the propylene formed according to reaction (3):

$$xCH_3CH=CH_2 \rightarrow (C_3H_6)_x \quad (3).$$

Although each of reactions (1)–(3) is acid catalyzed, the process of the invention is effective to decompose IPE according to reaction (1) while reducing IPA dehydration and propylene oligomerization. Preferably, the conditions used to effect IPE decomposition include a temperature of about 100° C. to about 320° C., such as about 200° C. to about 300° C., for example about 240° C. to about 280° C; a pressure of about 100 kPa to about 3550 kPa, such as about 400 kpa to about 1800 kPa, for example about 700 kPa to about 1500 kPa, a weight hourly space velocity (WHSV) of about 0.5 hr$^{-1}$ to about 10 hr$^{-1}$, such as about 3 hr$^{-1}$ to about 10 hr$^{-1}$, for example about 7 hr$^{-1}$. Conveniently, the feed to the catalyst includes water in addition to the IPE, with the molar ratio of water to IPE typically ranging from 0 to 3, such as about 0.5 to about 2, for example about 1.5.

In yet another practical embodiment, the ether-containing feed contains sec-butyl ether (SBE) and is produced as a by-product of the hydration of butene to produce sec-butanol. One possible method of disposal of the SBE is as a fuel, for example by addition to motor vehicle gasoline, but, not only may this be subject to environmental regulation, it also leads to a loss of butenes as a lower-valued component. Moreover, the SBE may not be readily isolatable as a single component stream by conventional separation techniques, and may form a mixture with close-boiling butene oligomers composed mostly of $C_8$ olefins formed by dimerization of the butenes. However, while the $C_8$ olefins, being highly branched, would make a good high-octane additive to gasoline, environmental regulation may require elimination of the SBE from this stream. Accordingly, a preferred decomposition pathway for SBE is by conversion to sec-butanol and 2-butene in a process that limits oligomerization of the butene formed and of the $C_8$ olefins present.

The catalyst compositions of the present invention are active for the selective conversion of SBE to sec-butanol and 2-butene with limited oligomerization of the resultant butenes and limited oligomerization/isomerization of any $C_8$ olefins present. At higher temperatures, some or all of the sec-butanol may be dehydrated to 2-butene according to a reaction of the type indicated above as reaction (2). In this embodiment, preferred ether decomposition conditions include a temperature of about 150° C. to about 275° C., a pressure of about 0 kPa to about 700 kPa, and a weight hourly space velocity (WHSV) of about 0.5 hr$^{-1}$ to about 10 hr$^{-1}$. Conveniently, the feed to the catalyst includes water in addition to the SBE, with the molar ratio of water to SBE typically ranging from 0 to 3, such as about 0.5 to about 2, for example about 1.5.

The processes of the invention may be conducted in a stationary or fluidized bed, and may take place continuously or batch-wise.

The processes of the invention may be conducted using pure ether feedstocks, or they may include a diluent such as nitrogen, argon, carbon dioxide, alkanes, and the like. In a preferred embodiment, water may be added together with the ether feed to minimize dehydration of the resultant alcohols.

The invention will now be more particularly described with reference to the following non-limiting Examples. Unless otherwise stated, all percentages are weight percent. The pH in the following examples was adjusted to the desired pH with the addition of either concentrated sulfuric acid or concentrated ammonium hydroxide depending on the initial pH of the gel.

EXAMPLE 1

(Comparative). MTBE Decomposition Over HF/Attapulgite

For comparison, the decomposition of MTBE over HF/Attapulgite was investigated in a fixed-bed microreactor. Two grams of an HF/Attapulgite catalyst, obtained from Engelhard, were loaded into a stainless steel reactor having an outside diameter of 0.375 inch (9.5 mm) and were dried with nitrogen gas ($N_2$) at 150° C. Anhydrous MTBE (99.8%, Aldrich) was fed to the reactor at the desired flow rate. During the course of this experiment, the catalyst performance at various temperatures, pressures and MTBE space velocities was investigated. Products were analyzed by on-line Gas Chromatography. Table I summarizes the conversion of MTBE, and the isobutene and methanol selectivities, over the catalyst of Example 1 at a pressure of 15 psig (204 kPa) and different reaction temperatures and space velocities. Table 2 summarizes the MTBE decomposition at 140° C., 15 psig (204 kPa), and WHSV=2.5 hr$^{-1}$ at various times on stream, showing rapid deactivation of the catalyst.

TABLE 1

| MTBE Decomposition over HF/Attapulgite | | | | | |
|---|---|---|---|---|---|
| | Temperature (° C.) | | | | |
| | 140 | | 150 | | |
| WHSV, hr$^{-1}$ | 2.0 | 2.5 | 2.5 | 3.5 | 5.0 |
| MTBE Conversion (%) | 91.4 | 88.7 | 93.3 | 91.0 | 78.1 |
| i-$C_4$ Selectivity (%) | | | | | |
| Isobutene | 99.22 | 99.43 | 99.29 | 99.39 | 99.57 |
| Isobutane | 0.003 | 0.002 | 0.003 | 0.002 | 0.002 |
| Diisobutene | 0.76 | 0.56 | 0.70 | 0.60 | 0.42 |
| Triisobutene | 0.02 | 0.01 | 0.01 | 0.01 | 0.002 |

TABLE 1-continued

MTBE Decomposition over HF/Attapulgite

|  | Temperature (° C.) | | | | |
|---|---|---|---|---|---|
|  | 140 | | 150 | | |
| WHSV, hr$^{-1}$ | 2.0 | 2.5 | 2.5 | 3.5 | 5.0 |
| Methanol Selectivity (%) | | | | | |
| MeOH | 99.91 | 99.92 | 99.90 | 99.92 | 99.95 |
| DME | 0.09 | 0.08 | 0.10 | 0.08 | 0.05 |

TABLE 2

MTBE Decomposition over HF/Attapulgite

| Days on Stream | 5 | 16 |
|---|---|---|
| MTBE Conversion (%) | 88.7 | 67.1 |
| i-C$_4$ Selectivity (%) | | |
| Isobutene | 99.43 | 99.74 |
| Isobutane | 0.002 | 0.00 |
| Diisobutene | 0.56 | 0.26 |
| Triisobutene | 0.01 | 0.00 |
| Methanol Selectivity (%) | | |
| MeOH | 99.92 | 99.96 |
| DME | 0.08 | 0.04 |

EXAMPLE 2

Synthesis of Ce/ZrO$_2$ (2 wt % Ce)

Five hundred grams of ZrOCl$_2$.8H$_2$O and 12.8 grams of cerium sulfate were dissolved with stirring in 3.0 liters of distilled water. Another solution containing 260 grams of concentrated NH$_4$OH and 3.0 liters of distilled water was prepared. Both solutions were heated to 60° C. and the heated solutions were combined at the rate of 50 ml/min using a nozzle mixer. The pH of the final composite was adjusted to 8 by the addition of concentrated ammonium hydroxide. The resultant slurry was then put in polypropylene bottles and placed in a steambox (100° C.) for 72 hours. The product formed was recovered by filtration, washed with excess water, and dried overnight at 85° C. The composition of the product was analyzed using X-ray fluorescence. The elemental analysis of the as-synthesized material was: Ce—2.61 weight %, Zirconium—62.2 weight %, and Sulfur—1.02 weight percent, corresponding to a mixed metal oxide of formula Zr$_m$Ce$_n$O$_q$S$_r$ in which m=1.0, n=0.03 and r=0.09. A sample of this catalyst was calcined to 700° C. in flowing air for 3 hours to produce a solid having the following elemental analysis: Ce—2.64 weight %, Zirconium—64.12 weight %, and Sulfur—0.69 weight percent, corresponding to a mixed metal oxide of formula Zr$_m$Ce$_n$O$_q$S$_r$ in which m=1.0, n=0.03 and r=0.06.

EXAMPLE 3

MTBE Decomposition Over Ce/ZrO$_2$

The decomposition of MTBE was investigated in a fixed-bed microreactor. Two grams of the calcined catalyst of Example 2 were loaded into a stainless steel reactor having an outside diameter of 0.375 inch (9.5 mm) and were dried with N$_2$ at 150° C. Anhydrous MTBE (99.8%, Aldrich) was fed to the reactor at the desired flow rate. During the course of this experiment, the performance of the catalyst at various temperatures, pressures, and MTBE space velocities was investigated. Products were analyzed by on-line Gas Chromatography. Table 3 summarizes the conversion of MTBE, and the isobutene and methanol selectivities, at a pressure of 15 psig (204 kPa) and different temperatures and space velocities. Table 4 summarizes the MTBE decomposition over the catalyst of Example 2 at 140° C., 15 psig (204 kPa) and a WHSV of 2.5 hr$^{-1}$ at various times on stream. Comparison with the data in Example 1 from the commercial HFA catalyst shows that the Ce/ZrO$_2$ catalyst has a much lower aging rate, thus demonstrating the higher stability of the catalyst.

TABLE 3

MTBE decomposition over Ce/ZrO$_2$

|  | Temperature (° C.) | | | | | |
|---|---|---|---|---|---|---|
|  | 140 | | | 150 | | |
| WHSV, hr$^{-1}$ | 2.5 | 4.0 | 5.0 | 2.5 | 4.0 | 5.0 |
| MTBE Conversion (%) | 91.8 | 91.5 | 91.0 | 94.7 | 94.2 | 93.9 |
| i-C$_4$ Selectivity (%) | | | | | | |
| Isobutene | 97.86 | 99.05 | 99.22 | 96.34 | 98.09 | 98.55 |
| Isobutane | 0.02 | 0.01 | 0.00 | 0.03 | 0.01 | 0.01 |
| Diisobutene | 2.03 | 0.94 | 0.77 | 3.45 | 1.85 | 1.41 |
| Triisobutene | 0.09 | 0.01 | 0.01 | 0.18 | 0.05 | 0.03 |
| Methanol Selectivity (%) | | | | | | |
| MeOH | 99.6 | 99.85 | 99.9 | 99.4 | 99.7 | 99.8 |
| DME | 0.4 | 0.15 | 0.1 | 0.6 | 0.3 | 0.2 |

TABLE 4

MTBE decomposition over Ce/ZrO$_2$

| Days on Stream | 5 | 10 | 31 |
|---|---|---|---|
| MTBE Conversion (%) | 91.8 | 91.9 | 92.0 |
| i-C$_4$ Selectivity (%) | | | |
| Isobutene | 97.86 | 98.41 | 98.34 |
| Isobutane | 0.02 | 0.01 | 0.006 |
| Diisobutene | 2.03 | 1.54 | 1.61 |
| Triisobutene | 0.09 | 0.04 | 0.05 |
| Methanol Selectivity (%) | | | |
| MeOH | 99.6 | 99.8 | 99.8 |
| DME | 0.4 | 0.2 | 0.2 |

As the data in Tables 2 and 4 show, the Ce/ZrO$_2$ catalyst has negligible deactivation over the current run length achievable with the HFA catalyst and the reduction in reactor down-time resulting from fewer catalyst change-outs would further increase production capacity.

EXAMPLE 4

Performance Comparison of Ce/ZrO$_2$ and HF/Attapulgite

Table 5 compares the MTBE decomposition over the catalyst of Example 2 with that of the commercial HFA catalyst of Example 1 at conditions (i.e., space velocities) chosen to give substantially identical performance. The data of Table 5 suggest that the Ce/ZrO$_2$ catalyst could replace the HFA catalyst to give the same product spectrum with a 2.5 fold increase in production capacity.

TABLE 5

Performance Comparison of Ce/ZrO$_2$ and HF/Attapulgite

| Catalyst<br>WHSV, hr$^{-1}$ | Ce/ZrO$_2$<br>5 | HFA<br>2 |
|---|---|---|
| MTBE Conversion (%) | 91.0 | 91.4 |
| i-C$_4$ Selectivity (%) | | |
| Isobutene | 99.22 | 99.22 |
| Isobutane | 0.005 | 0.003 |
| Diisobutene | 0.77 | 0.76 |
| Triisobutene | 0.01 | 0.01 |
| Methanol Selectivity (%) | | |
| MeOH | 99.89 | 99.91 |
| DME | 0.11 | 0.09 |

EXAMPLE 5

Synthesis of FeO$_x$/WO$_y$/ZrO$_2$

Five hundred grams of ZrOCl$_2$.8H$_2$O were dissolved with stirring in 3.0 liters of distilled water. To this solution was added 7.6 grams of FeSO$_4$.7H$_2$O. Another solution containing 260 grams of concentrated NH$_4$OH, 54 grams of (NH$_4$)$_6$H$_2$W$_{12}$O$_{40}$.xH$_2$O and 2940 ml of distilled water was prepared. Both solutions were heated to 60° C. and the heated solutions were combined at the rate of 50 ml/min using a nozzle mixer. The pH of the final composite was adjusted to approximately 9 by the addition of concentrated ammonium hydroxide. The resultant slurry was then put in polypropylene bottles and placed in a steambox (100° C.) for 72 hours. The product formed was recovered by filtration, washed with excess water, and dried overnight at 85° C. The composition of the product was analyzed using X-ray fluorescence. The elemental analysis for the as-synthesized product was: W—18.1 weight %, Zirconium—54.3 weight %, Iron—0.58 weight %, and Sulfur—0.07 weight percent, corresponding to a mixed metal oxide of formula Zr$_m$W$_n$Fe$_p$ O$_q$S$_r$, in which m=1.0, n=0.16, p=0.02 and r is less than 0.005. A sample of this catalyst was calcined to 500° C. in flowing air for 3 hours.

EXAMPLE 6

MTBE Decomposition Over FeO$_x$/WO$_y$/ZrO$_2$

The decomposition of MTBE was investigated in a fixed-bed microreactor. One gram of the calcined catalyst of Example 5 was loaded into a stainless steel reactor having an outside diameter of 0.375 inch (9.5 mm) and was dried with N$_2$ at 150° C. Anhydrous MTBE (99.8%, Aldrich) was fed to the reactor at the desired flow rate. During the course of this experiment, the catalyst's performance at various temperatures, pressures, and MTBE space velocities was investigated. Products were analyzed by on-line Gas Chromatography. Table 6 summarizes the conversion of MTBE, and the isobutene and methanol selectivities, at a pressure of 15 psig (204 kPa) and different temperatures and space velocities. Table 7 summarizes the MTBE decomposition over the catalyst of Example 5 at 140° C., 15 psig (204 kPa) and a WHSV of 2.5 hr$^{-1}$ at various times on stream. Comparison with data from the commercial HFA catalyst (Table 2) shows that the FeO$_x$/WO$_y$/ZrO$_2$ catalyst has a much lower aging rate, thus demonstrating the higher stability of the catalyst.

TABLE 6

MTBE decomposition over FeO$_x$/WO$_y$/ZrO$_2$

| | Temperature (° C.) | | | | | |
|---|---|---|---|---|---|---|
| | 140 | | | 150 | | |
| WHSV, hr$^{-1}$ | 2.5 | 5.0 | 7.5 | 2.5 | 5.0 | 7.5 |
| MTBE Conversion (%) | 90.0 | 78.4 | 66.2 | 92.9 | 87.9 | 80.8 |
| i-C$_4$ Selectivity (%) | | | | | | |
| Isobutene | 99.88 | 99.91 | 99.93 | 99.89 | 99.91 | 99.91 |
| Isobutane | 0.00 | 0.00 | 0.00 | 0.00 | 0.00 | 0.00 |
| Diisobutene | 0.11 | 0.08 | 0.06 | 0.11 | 0.09 | 0.07 |
| Triisobutene | 0.00 | 0.01 | 0.01 | 0.00 | 0.00 | 0.01 |
| Methanol Selectivity (%) | | | | | | |
| MeOH | 99.72 | 99.85 | 99.90 | 99.67 | 99.77 | 99.83 |
| DME | 0.28 | 0.15 | 0.10 | 0.33 | 0.23 | 0.17 |

TABLE 7

MTBE decomposition over FeO$_x$/WO$_y$/ZrO$_2$

| Days on Stream | 1 | 12 | 21 |
|---|---|---|---|
| MTBE Conversion (%) | 90.0 | 80.9 | 83.6 |
| i-C$_4$ Selectivity (%) | | | |
| Isobutene | 99.88 | 99.91 | 99.87 |
| Isobutane | 0.00 | 0.00 | 0.00 |
| Diisobutene | 0.11 | 0.09 | 0.13 |
| Triisobutene | 0.00 | 0.00 | 0.00 |
| Methanol Selectivity (%) | | | |
| MeOH | 99.72 | 99.78 | 99.76 |
| DME | 0.28 | 0.22 | 0.24 |

EXAMPLE 7

Synthesis of Ce/ZrO$_2$ (30 wt. % Ce)

One hundred and twenty-five grams of ZrOCl$_2$.8H$_2$O and 52 grams of cerium sulfate were dissolved with stirring in 1.5 liters of distilled water. Another solution containing 65 gram of concentrated NH$_4$OH and 1.5 liters of distilled water was prepared. These two solutions were combined at room temperature at the rate of 50 ml/min using a nozzle mixer. The pH of this combined mixture was adjusted to 8 with the addition of concentrated sulfuric acid (H$_2$SO$_4$). This slurry was then put in polypropylene bottles and placed in a steambox (100° C.) for 72 hours. The product formed was recovered by filtration, washed with excess water, and dried overnight at 85° C. The composition of the product was analyzed using X-ray fluorescence. The elemental analysis for the as-synthesized material was: Ce—26 weight %, Zirconium—47 weight %, and Sulfur—1.54 weight percent, corresponding to a mixed metal oxide of formula Zr$_m$Ce$_n$O$_q$S$_r$, in which m=1.0, n=0.36 and r=0.19. A portion of this material was calcined to 700° C. in flowing air for 3 hours to produce a solid containing a nominal 30% Ce on zirconia. Elemental analyses indicated that the cerium content was 26% by weight.

EXAMPLE 8

IPE Decomposition Over Ce/ZrO$_2$

The decomposition of isopropyl ether (IPE) was investigated in a fixed-bed microreactor. 0.5 gram of the calcined catalyst of Example 7 was loaded into a stainless steel reactor having an outside diameter of 0.375 inch (9.5 mm) and was dried with N$_2$ at 200° C. Isopropyl ether (99%, Aldrich) was fed to the reactor at a WHSV of 6 hr$^{-1}$. Reactor pressure was atmospheric. Products were analyzed by on-line Gas Chromatography. Table 8 summarizes the performance of the catalyst, at different reaction temperatures, using the following definitions:

IPE Conversion=(IPE$_{product}$−IPE$_{feed}$)/IPE$_{feed}$ where IPE$_{product}$ is the wt % of IPE in the product and where IPE$_{feed}$ is the wt % of IPE in the feed;

IPA Conversion=(IPA$_{theoretical}$−IPA$_{product}$)/(IPA$_{theoretical}$)

where IPA$_{theoretical}$=theoretical IPA produced stoichiometrically from the IPE decomposed;

where IPA$_{product}$ is the wt % of IPA in the product;

IPA Selectivity=IPA$_{product}$/(IPA$_{theoretical}$)

IPA Yield (per pass)=IPE Conversion×IPA Selectivity.

TABLE 8

IPE Decomposition over Ce/ZrO$_2$

| Temperature (° C.) | 200 | 210 |
|---|---|---|
| Time on Stream (hr) | 21 | 61 |
| Product Composition (wt %) | | |
| Propylene | 41.06 | 55.69 |
| Isopropanol | 31.09 | 27.21 |
| Isopropyl ether | 24.16 | 10.00 |
| C$_6$'s | 0.07 | 0.09 |
| C$_9$'s | 0.03 | 0.00 |
| C$_{12}$'s | 0.00 | 0.00 |
| Water | 3.55 | 6.96 |
| IPE Conversion (%) | 75.8 | 90.0 |
| IPA Conversion (%) | 30.3 | 48.6 |
| Propylene Selectivity (%) | 99.7 | 99.8 |
| IPA Selectivity (%) | 69.8 | 51.4 |
| IPA Yield | 52.9 | 46.3 |

As the data of Table 8 show, the ceria-zirconia catalyst achieves high conversion of IPE with low conversion of IPA. Production of propylene dimers and trimers is low, with exit concentrations on the order of 800 ppm for the dimer.

By raising the temperature, it is possible to achieve full conversion of IPE, but this comes at the cost of increased conversion of IPA to propylene. The advantages of full conversion of IPE to propylene include a reduction in separation complexity of the resulting stream, as propylene can be more readily separated using a flash drum. However, this would require reconversion of the recycled propylene into IPA. Partial conversion of IPE, as shown in Table 8, allows recovery of IPA directly. Direct recovery of IPA would require a more complex separation device that would also recover unreacted IPE, which could then be recycled to extinction in the IPE decomposition reactor. The catalysts of this invention allow for both modes of operation of the IPE decomposition reactor, and the preferred conditions for IPA recovery would be determined based on an economic assessment.

EXAMPLE 9

SBE Decomposition Over 30% Ce/ZrO$_2$

The decomposition of sec-butyl ether (SBE) was investigated in a fixed-bed microreactor. 0.5 gram of the calcined catalyst of Example 7 was loaded into a stainless steel reactor having an outside diameter of 0.375 inch (9.5 mm) and was dried with N$_2$ at 200° C. A feed stream containing 53.4% sec-butyl ether (SBE), with the balance being mostly C8 olefins, was fed to the reactor at a WHSV of 5 hr$^{-1}$. Reactor pressure was 50 psig (446 kPa). Products were analyzed by on-line Gas Chromatography. Table 9 summarizes the conversion of SBE, the conversion of SBA and the butane selectivities at different reaction temperatures.

TABLE 9

SBE Decomposition over 30% Ce/ZrO$_2$

| Temperature (° C.) | 200 | 210 | 220 |
|---|---|---|---|
| Time on Stream (hr) | 23 | 47 | 65 |
| Product Composition (wt %) | | | |
| 1-butene | 0.60 | 0.63 | 0.65 |
| Isobutene | 2.38 | 3.24 | 3.91 |
| Trans-2-butene | 12.96 | 16.96 | 18.96 |
| Cis-2-Butene | 11.33 | 15.11 | 17.00 |
| Sec-Butanol | 11.13 | 5.78 | 2.00 |
| SBE | 8.80 | 1.31 | 1.26 |
| Total C$_8$ olefins | 48.83 | 50.49 | 48.69 |
| Water | 3.33 | 5.72 | 6.69 |
| SBE Conversion (%) | 83.5 | 97.6 | 97.6 |
| SBA Conversion (%) | 56.2 | 80.5 | 93.3 |
| SBA Selectivity (%) | 43.7 | 19.4 | 6.7 |

As the data of Table 9 show, raising the temperature promotes higher conversion of SBE using the ceria zirconia catalyst. Analysis of the C$_8$ isomers showed that the concentrations of the 2,3-dimethyl-1-hexene and 2,3,3-trimethyl-1-pentene did not vary significantly with time on-stream or temperature, suggesting that there is little isomerization taking place among these isomers.

EXAMPLE 10

Synthesis of Ce/ZrO$_2$ (24 wt. % Ce)

One hundred and twenty-five grams of ZrOCl$_2$.8H$_2$O and 43 grams of cerium sulfate were dissolved with stirring in 1.5 liters of distilled water. Another solution containing 95 grams of concentrated NH$_4$OH and 1.5 liters of distilled water was prepared. These two solutions were combined at room temperature at the rate of 50 ml/min using a nozzle mixer. The pH of this combined mixture was adjusted to 8 with the addition of concentrated sulfuric acid. This slurry was then put in polypropylene bottles and placed in a steambox (100° C.) for 72 hours. The product formed was recovered by filtration, washed with excess water, and dried overnight at 85° C. The material's composition was analyzed using X-ray fluorescence. The elemental analysis of the as-synthesized material was: Ce—23.2 weight %, Zirconium—46.3 weight %, and Sulfur—2.82 weight percent, corresponding to a mixed metal oxide of formula Zr$_m$Ce$_n$O$_q$S$_r$, in which m=1.0, n=0.33 and r=0.35. A portion of this material was calcined to 700° C. in flowing air for 3 hours to produce a solid containing a nominal 24% Ce on zirconia.

EXAMPLE 11

SBE Decomposition and SBA Recovery Over 24% Ce/ZrO$_2$

The decomposition of SBE and recovery of SBA were investigated in a fixed-bed microreactor. 0.5 gram of the calcined catalyst of Example 10 was loaded into a stainless steel reactor having an outside diameter of 0.375 inch (9.5 mm) and was dried with N$_2$ at 200° C. A feed stream containing 53.4% sec-butyl ether (SBE) was fed to the reactor at a WHSV of 5 hr$^{-1}$. Water (HPLC grade, Aldrich Chemical Company) was co-fed to the reactor at a SBE/H$_2$O molar ratio of 1.0. Reactor pressure was 50 psig (446 kPa). Products were analyzed by on-line Gas Chromatography. Table 10 summarizes the conversion of SBE, the conversion of SBA, and the butane selectivities, at different reaction temperatures.

TABLE 10

SBE Decomposition and SBA Recovery over 24% Ce/ZrO$_2$

| Temperature (° C.) | 200 | 210 |
|---|---|---|
| Time on Stream (hr) | 53 | 65 |
| Product Composition (wt %) | | |
| 1-butene | 0.54 | 0.55 |
| Isobutene | 1.17 | 1.87 |
| Trans-2-butene | 6.27 | 9.47 |
| Cis-2-Butene | 5.47 | 9.00 |
| Sec-Butanol | 8.19 | 15.37 |
| SBE | 23.90 | 7.81 |
| Total C$_8$ olefins | 45.38 | 46.29 |
| Water | 8.58 | 9.08 |
| SBE Conversion (%) | 51.6 | 84.2 |
| SBA Conversion (%) | 43.6 | 35.1 |
| SBA Selectivity (%) | 56.4 | 64.8 |

The data of Table 10 show that co-feeding water suppresses the dehydration of SBA to butene, thereby increasing the selectivity towards SBA.

EXAMPLES 12 AND 13

Comparative

Samples of commercial ceria/zirconia having a nominal 15 wt % ceria content (Example 12, Elemental analysis: Ce—11.5 weight %, Zirconium—59.95 weight %, and Sulfur—0.066 weight percent, corresponding to a mixed metal oxide of formula Zr$_m$Ce$_n$O$_q$S$_r$ in which m=1.0, n=0.12 and r=0.01) and a nominal 17.5 wt % ceria content (Example 13, Ce—14.2 weight %, Zirconium—57.46 weight %, and Sulfur—0.052 weight percent, corresponding to a mixed metal oxide of formula Zr$_m$Ce$_n$O$_q$S$_r$ in which m=1.0, n=0.16 and r=0.01) were obtained from Grace Davison and Magnesium Electron Inc., respectively. 0.5 gram of each sample was loaded into a fixed-bed microreactor and used as a catalyst in the decomposition of isopropyl ether (IPE) according to the procedure of Example 8. In each case the reactor was run for 24 hours, but the IPE conversion was <1% throughout and the IPA yield was essentially zero. Thus both commercial materials were inactive for IPE decomposition.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

We claim:

1. A process for selectively converting a dialkyl ether to the corresponding alkene and alkanol, the process comprising contacting a feed containing at least one dialkyl ether with a catalyst comprising an acidic mixed metal oxide having the following composition:

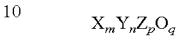

where X is at least one metal selected from Group 4 of the Periodic Table of Elements, Y is at least one metal selected from Group 3 (including the Lanthanides and Actinides) and Group 6 of the Periodic Table of Elements and Z is at least one metal selected from Groups 7, 8, and 11 of the Periodic Table of Elements; m, n, p and q are the atomic ratios of their respective components and, when m is 1, n is from about 0.01 to about 0.75, p is from 0 to about 0.1, and q is the number of oxygen atoms necessary to satisfy the valence of the other components.

2. The process of claim 1, wherein n is from about 0.02 to about 0.6.

3. The process of claim 1, wherein p is from 0 to about 0.05.

4. The process of claim 1, wherein said at least one metal selected from Group 4 of the Periodic Table of Elements comprises zirconium.

5. The process of claim 1, wherein said at least one metal selected from Group 3 and Group 6 of the Periodic Table of Elements comprises cerium.

6. The process of claim 1, wherein said at least one metal selected from Group 3 and Group 6 of the Periodic Table of Elements comprises molybdenum or tungsten.

7. The process of claim 1, wherein said at least one metal selected from Groups 7, 8, and 11 of the Periodic Table of Elements is selected from iron, manganese, and copper.

8. The process of claim 1, wherein said mixed metal oxide also contains sulfur, and has the composition X$_m$Y$_n$Z$_p$O$_q$S$_r$ where X, Y, Z, m, n, p and q have the same meaning as in the preceding claims, and S is sulfur and r is the atomic ratio of sulfur.

9. The process of claim 8, wherein said sulfur is present in an amount up to 5% by weight of the total mixed metal oxide composition.

10. The process of claim 8, wherein said sulfur is present in an amount up to 1% by weight of the total mixed metal oxide composition.

11. The process of claim 8, wherein said sulfur is present as sulfate.

12. The process of any of claim 8, wherein, when m is 1, r is from 0.03 to 0.5.

13. The process of claim 12, wherein r is from 0.04 to 0.4.

14. The process of claim 12, wherein r is from 0.05 to 0.36.

15. The process of claim 8, wherein X is zirconium, Y is Cerium and p=0.

16. The process of claim 1, wherein said contacting is effected under conditions including a temperature of about 50° C. to about 320° C., a pressure of about 0 kPa to about 3500 kPa and a weight hourly space velocity (WHSV) of about 0.1 hr$^{-1}$ to about 50 hr$^{-1}$.

17. The process of claim 1, wherein said contacting is effected under conditions including a temperature of about 100® C. to about 275° C., a pressure of about 0 kPa to about 2400 kPa and a weight hourly space velocity (WHSV) of about 0.5 hr$^{-1}$ to about 10 hr$^{-1}$.

18. The process of claim 1, wherein said ether is an alkyl tert-alkyl ether.

19. The process of claim 18, wherein said ether is methyl tert-butyl ether (MTBE) or tert-amyl methyl ether (TAME).

20. The process of claim 19, wherein said contacting is effected under conditions including a temperature of about 100° C. to about 200° C., a pressure of about 0 kPa to about 1000 kPa and a weight hourly space velocity (WHSV) of about 1 $hr^{-1}$ to about 10 $hr^{-1}$.

21. The process of claim 1, wherein said ether is isopropyl ether or sec-butyl ether.

22. The process of claim 21, wherein said feed also contains water.

23. The process of claim 22, wherein said feed also contains water in an amount such that the molar ratio of water to ether is up to 3.

24. The process of claim 21, wherein said feed also contains water in an amount such that the molar ratio of water to ether is from about 0.5 to about 2.

25. The process of claim 21, wherein said ether is isopropyl ether and said contacting is effected under conditions including a temperature of about 200° C. to about 300° C., a pressure of about 400 kPa to about 1800 kPa and a weight hourly space velocity (WHSV) of about 3 $hr^{-1}$ to about 10 $hr^{-1}$.

26. The process of claim 21, wherein said ether is sec-butyl ether and said contacting is effected under conditions including a temperature of about 150° C. to about 275° C., a pressure of about 0 kPa to about 700 kPa and a weight hourly space velocity (WHSV) of about 0.5 $hr^{-1}$ to about 10 $hr^{-1}$.

27. A process for selectively converting a dialkyl ether to the corresponding alkene and alkanol comprising contacting a feed containing at least one dialkyl ether with a catalyst comprising a mixed metal oxide consisting essentially of at least one metal selected from Group 4 of the Periodic Table of Elements and at least one metal selected from Group 3 (including the Lanthanides and Actinides) and Group 6 of the Periodic Table of Elements and which is produced by co-precipitating oxide precursors of said metals from a liquid medium and then calcining the co-precipitate.

28. The process of claim 27, wherein said calcining is conducted at a temperature of at least 400° C.

29. The process of claim 27, wherein said calcining is conducted at a temperature of at least 500° C.

30. The process of claim 27, wherein said calcining is conducted at a temperature of about 500° C. to about 800° C.

31. The process of claim 27, wherein said oxide precursors are precipitated from said liquid medium at a pH at or below 9.

32. The process of claim 27, wherein said oxide precursors are precipitated from said liquid medium at a pH of about 6 to about 9.

33. The process of claim 27, wherein said liquid medium contains sulfate ions.

34. The process of claim 27, wherein said at least one metal selected from Group 4 of the Periodic Table of Elements comprises zirconium.

35. The process of claim 34, wherein said liquid medium contains zirconium nitrate.

36. The process of claim 27, wherein said at least one metal selected from Group 3 of the Periodic Table of Elements comprises cerium.

37. The process of claim 36, wherein said liquid medium contains a cerium sulfate.

38. The process of claim 27, wherein said at least one metal selected from Group 6 of the Periodic Table of Elements comprises molybdenum or tungsten.

39. The process of claim 27, wherein said mixed metal oxide also contains a further metal selected from Groups 7, 8 and 11 of the Periodic Table of Elements.

40. The process of claim 39, wherein said further metal is selected from iron, manganese and copper.

41. The process of claim 27, wherein said ether is an alkyl tert-alkyl ether.

42. The process of claim 41, wherein said ether is methyl tert-butyl ether (MTBE) or tert-amyl methyl ether (TAME).

43. The process of claim 27, wherein said ether is isopropyl ether or sec-butyl ether.

44. The process of claim 27, wherein said contacting is effected under conditions including a temperature of about 50° C. to about 320° C., a pressure of about 0 kPa to about 3500 kPa and a weight hourly space velocity (WHSV) of about 0.1 $hr^{-1}$ to about 50 $hr^{-1}$.

45. The process of claim 27, wherein said contacting is effected under conditions including a temperature of about 100° C. to about 275° C., a pressure of about 0 kPa to about 2400 kPa and a weight hourly space velocity (WHSV) of about 0.5 $hr^{-1}$ to about 10 $hr^{-1}$.

* * * * *